United States Patent [19]

Krause et al.

[11] Patent Number: 5,188,940
[45] Date of Patent: Feb. 23, 1993

[54] METHOD OF DETERMINING THE TOTAL FIBRINOLYTIC ACTIVITY IN THE PLASMA

[75] Inventors: Jürgen Krause, Warthausen; Walter Haarmann, Biberach, both of Fed. Rep. of Germany

[73] Assignee: Dr. Karl Thomae GmbH, Fed. Rep. of Germany

[21] Appl. No.: 463,177

[22] Filed: Jan. 10, 1990

[30] Foreign Application Priority Data

Jan. 10, 1989 [DE] Fed. Rep. of Germany ....... 3900493

[51] Int. Cl.$^5$ ............................................. C12Q 1/56
[52] U.S. Cl. ........................................ 435/13; 436/69
[58] Field of Search ............................. 436/69; 435/13

[56] References Cited

U.S. PATENT DOCUMENTS 5,071,745 12/1991 Triscott et al. ................... 435/13 X

FOREIGN PATENT DOCUMENTS

3502878 7/1986 Fed. Rep. of Germany ........ 435/13

Primary Examiner—Jill A. Johnston
Attorney, Agent, or Firm—David E. Frankhouser; Daniel Reitenbach; Mary-Ellen M. Timbers

[57] ABSTRACT

A method of determining the total fibrinolytic activity in plasma, is characterized in that
a) a quantity of fibrin sufficient to produce turbidity is added to a dilute platelet poor plasma sample or is produced in situ and the time dependent change in turbidity or the time-dependent formation of fibrin cleavage products is measured; or
b) a chromogenic plasmin substrate and a quantity of fibrin, fibrinogen cleavage products or an enzyme which produces fibrin in situ, insufficient to produce turbidity, is added to a dilute platelet poor plasma sample and the time dependent color formation is measured.

3 Claims, 6 Drawing Sheets

| Measurement of time in mins | ng/ml rt-PA | | | | | | | | | | | | |
|---|---|---|---|---|---|---|---|---|---|---|---|---|---|
| | 1000 | 800 | 600 | 400 | 200 | 100 | 80 | 60 | 40 | 20 | 10 | 8 | 6 | 4 |
| PPP undiluted | | | | | | | | | | | | | | |
| 50% Lysis | 3.50 | 3.80 | 4.80 | 5.60 | 8.75 | 19.72 | 24.50 | 29.40 | 57.10 | 79.80 | >150 | n.d. | n.d. | n.d. |
| End of lysis | 4.30 | 5.50 | 6.70 | 8.50 | 15.73 | 30.87 | 35.79 | 46.73 | 75.37 | >150 | >150 | n.d. | n.d. | n.d. |
| PPP 1:10 diluted | | | | | | | | | | | | | | |
| 50% Lysis | 3.26 | 3.55 | 3.98 | 5.07 | 6.77 | 8.78 | 9.91 | 11.87 | 14.84 | 22.57 | 34.20 | 39.55 | 48.88 | 62.58 |
| End of Lysis | 5.47 | 6.01 | 6.56 | 8.39 | 11.08 | 14.11 | 15.84 | 19.04 | 23.10 | 34.79 | 50.72 | 57.46 | 69.83 | 89.70 | n.d. = not determined

FIG. 6

METHOD OF DETERMINING THE TOTAL FIBRINOLYTIC ACTIVITY IN THE PLASMA

BACKGROUND OF THE INVENTION

DE-A-3,502,878 describes a method of determining the fibrinolytic state of plasma, which is characterised in that a) a sufficient quantity of fibrin to produce turbidity is added to a native plasma sample or generated in situ and the turbidity or the fibrin cleavage products formed is or are measured or b) a chromogenic plain substrate and a quantity of fibrin, fibrinogen cleavage products or an enzyme which produces fibrin in situ, insufficient to produce turbidity, are added to the native plasma sample and the colour formed is measured.

The method characterised above is intended to enable the hyperfibrinolytic activity of the plasma to be determined in a "relatively short time", which would be useful particularly when monitoring fibrinolysis therapy. A specific quantity of plasminogen activator is expediently added to the plasma which is to be investigated, whilst preferably therapeutically acceptable concentrations of plasminogen activators are used. In this embodiment, the possible reactivity of the plasma in the presence of defined amounts of plasminogen activator is therefore determined. In this way it is possible to establish how the fibrinolytic state of the plasma changes as a result of the addition of the therapeutic agents provided for fibrinolysis therapy, such as t-PA, urokinase, prourokinase, streptokinase or a derivative thereof.

In practice, however, it has been found that the method of determination described above is much too time-consuming and insufficiently sensitive for the acute monitoring of lysis therapy, particularly using low concentrations of a plasminogen activator such as t-PA, e.g. having an rt-PA content of between 2 ng/ml and 1000 ng/ml, preferably between 2 ng/ml and 100 ng/ml.

The aim of the present invention is therefore to provide a global fibrinolysis test which can be carried out automatically and evaluated photometrically, which avoids the disadvantages of the method described above and, more particularly, rapidly gives results which reliably reflect the state in vivo.

According to the invention this aim is achieved by using dilute platelet poor plasma (PPP=platelet poor plasma) instead of native plasma.

DESCRIPTION OF THE INVENTION

The method according to the invention for determining the overall fibrinolytic activity in the plasma is thus characterised in that a) a quantity of fibrin sufficient to produce turbidity is added to a dilute platelet poor plasma sample or this fibrin is generated in situ and the change in turbidity as a function of time or the formation of fibrin cleavage products as a function of time is measured or b) a chromogenic plain substrate and a quantity of fibrin, fibrinogen cleavage products or an enzyme which generates fibrin in situ, insufficient to produce turbidity, are added and the colour formation as a function of time is measured.

The term "turbidity measurement" within the scope of the invention means the measurement of the increase and/or decrease in turbidity per unit of time, the measurement of time until the peak turbidity is reached or the measurement of time until a specific decrease or increase in turbidity is achieved, in each case based on the turbidity peak. A combination of the possible methods of measurement may also be used.

The colour may be measured by kinetic monitoring of colour formation, by determining the change in extinction per unit of time. Similarly, the extinction achieved after a predetermined time may be measured or the colour forming reaction may be stopped after a given time and then the colour produced is measured at a convenient time later on.

The fibrin cleavage products formed may be measured using standard commercial test reagents and methods. Examples include the Staphylococci clumping test (manufactured by Boehringer Mannheim GmbH) or immunological methods such as those using antibody-coated latex particles (manufactured by Wellcome Corp.).

The colour forming reaction may be stopped by the addition of suitable inhibitors, preferably plain inhibitors or acids such as acetic or citric acid. Preferably, the time taken to achieve a certain extinction is measured.

The process according to the invention defined hereinbefore yields a measurement of the hyperfibrinolytic activity of plasma. Plasminogen activators already present in the plasma or formed therein initiate the reaction. This embodiment of the method according to the invention is particularly suitable for monitoring fibrinolysis therapy. It can be used to determine how the fibrinolytic state of the native plasma is changing in the course of treatment.

According to another embodiment of the method according to the invention, a specific quantity of plasminogen activator is also added to the blood or plasma, preferably using therapeutically acceptable concentrations. In this embodiment of the method the possible reactivity of the plasma is measured in the presence of defined quantities of plasminogen activator. This is particularly important for plotting a calibration curve and starting fibrinolysis therapy. It is possible to establish how the fibrinolytic state of the plasma changes when the therapeutic agents provided for fibrinolysis therapy, such as t-PA, urokinase, prourokinase, Streptokinase or derivatives thereof, are added.

According to a preferred embodiment the fibrin is produced in situ by the addition of thrombin or a thrombinlike enzyme such as batroxobin or arvin.

The fibrinogen cleavage products used are preferably those obtained by treating fibrinogen with bromocyanogen (I. H. Verheijen, Thromb. Haemostas 48, 266–269 (1982)). It is preferred to use concentrations of from 10 to 150 µg/ml.

Fibrin monomers are produced by treating fibrinogen with batroxobin, inactivating the batroxobin with diisopropylfluorophosphate, removing and then dissolving the fibrinolate in 1- to 3-molar urea solution. Concentrations of 1 to 100 µg/ml of fibrin monomer are preferably used.

The chromogenic plain substrate used may be any plain substrate from which a group suitable for colour formation can be cleaved under the effect of plain. The colour forming groups in question are both those which can be measured directly photometrically such as nitroaniline, dinitroaniline and derivatives thereof as well as those compounds which bring about colour formation by reacting with another component.

In the embodiment of the method according to the invention in which a plasminogen activator is added, the plasminogen activator used may be, for example, t-PA, prourokinase, urokinase, Streptokinase or a derivative thereof. A preferred chromogenic plain substrate is Tos-Gly-Pro-Lys-p-nitroaniline.

The method according to the invention may be carried out at any constant temperature between about 20° and 40° C., but preferably under physiological conditions, i.e. at 37° C.

The method according to the invention is expediently carried out as follows:

The method of determination according to the invention preferably uses dilute PPP, the dilution range expediently being between 1:5 and 1:25, but preferably between 1:8 and 1:15.

The platelet poor plasma to be investigated is prepared by methods known per se, e.g. by centrifuging the citrated blood or EDTA blood taken for investigation, expediently at 3,000 to 4,000×g, but preferably at 3,000 to 3,500×g and within 10 minutes.

The diluents used may be the diluents conventionally used for activity measurement in plasma, especially isotonic diluents such as physiological saline solution or buffered diluent such as tris buffer, NaCl buffer or HEPES buffer, e.g. 0.1 M tris buffer pH 7.4, 0.2 M tris buffer pH 7.4, 0.1 M HEPES buffer pH 7.4 or 0.9% NaCl buffer.

The diluents mentioned hereinbefore may additionally contain other conventional adjuvants, e.g. a complex forming agent such as 0.02% by weight EDTA, a surface-active substance such as 0.1% by weight Tween 80 and/or one percent by weight blood serum albumin.

However, a diluent which is preferred according to the invention is one of the above-mentioned diluents which contains polyethyleneglycol with a molar weight of 8,000 to 35,000, but preferably from 9,000 to 12,500, in a concentration of 1 to 5 percent by weight, but preferably two percent by weight. By means of the used polyethyleneglycol in accordance with the invention an increase in opacity in the samples being tested can be achieved whilst at the same time the rate of clot formation is not reduced and the rate of clot retraction is not too high preferably when using polyethyleneglycol with a molar weight of 9,000 to 12,500.

Of course, the required amount of polyethyleneglycol with a molecular weight of 8,000 to 35,000, preferably 9,000 to 12,500, may subsequently be added to an already suitably diluted plasma sample until a concentration of 1 to 5 percent by weight is achieved. However, when it is added subsequently polyethylene-glycol with a molecular weight of 9,000 to 12,500 is preferably added up to a concentration of only 1.5 percent by weight.

The PPP thus diluted and already containing plasminogen activator, preferably rt-PA, in the various dilution steps corresponding to the concentration series selected, is coagulated with a thrombin-like enzyme such as batroxobin. The clear uncoagulated PPP becomes cloudy during the coagulation, in doing so the turbidity increases as coagulation progresses. The addition of plasminogen activators before the start of coagulation has the effect of lysing the coagulated material after a coagulation peak has been reached. Lysis is accompanied by a reduction in turbidity. The end of lysis is characterised by the attainment of the initial value.

In order to determine the standard curve which is plotted from platelet poor plasma before the start of therapy, for example 0.1 ml of PPP are diluted with 0.9 ml of a suitable diluent which contains polyethyleneglycol and after mixing the mixture is incubated for 5 minutes at 7° C. Then, for example, 50 µl of batroxobin are added and after mixing the change in turbidity is recorded photometrically at a wavelength of 340 nm and at 37° C. Using the standard curve it is possible to determine the concentration of plasminogen activator corresponding to the fibrinolytic activity in the plasma from the time taken to achieve 50% lysis. The maintenance of a constant temperature throughout an entire series of measurements is critical since the enzymatic reaction of which lysis is based is temperature-dependent. As the temperature falls, the speed of lysis is also reduced and values of measurements taken at different times and at different temperatures cannot be correlated with one another.

The evaluation here is based on the correlation that the time taken to achieve 50% lysis is in inverse proportion to the concentration of plasminogen activator in the sample. The measurement of fibrinolytic activity is the time from the start of coagulation until 50% lysis is achieved, in relation to the peak coagulation (see FIG. 1). The values for the total activity obtained from calculations based on the achievement of 50% lysis correlate very well with values obtained on the basis of the end of lysis. Therefore it is sensible to end the test after 50% lysis has been achieved since this significantly reduces the time taken for each individual measurement and for the method as a whole to be carried out.

Figure 2A:
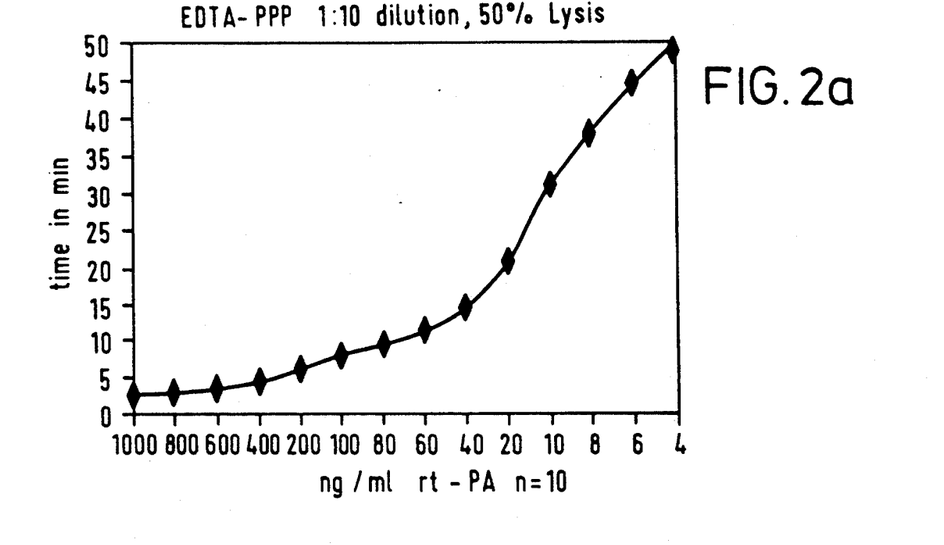
FIG. 2a shows a standard curve of fibrinolytic activity (50%lysis) of rt-PA in 1:10 diluted PPP from EDTA blood.
Figure 2B:
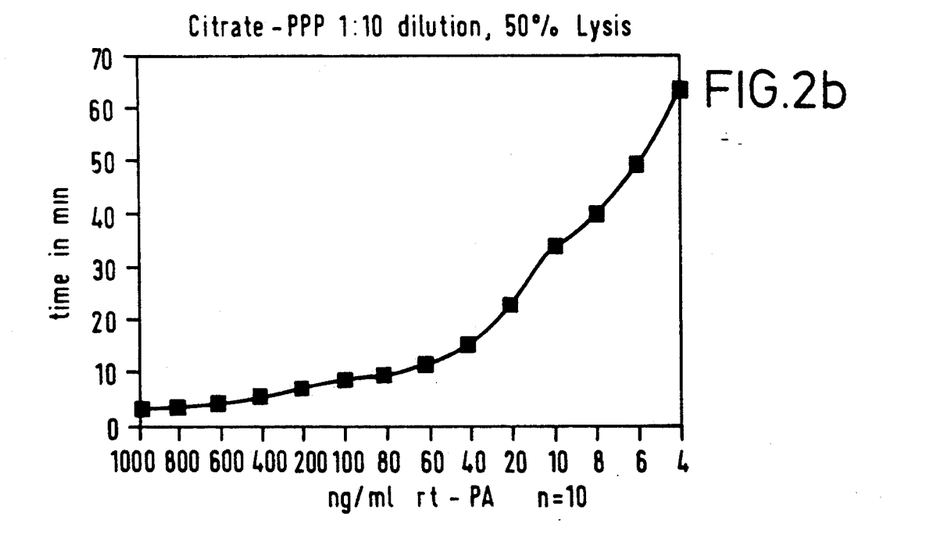
FIG. 2b shows a standard curve of fibrinolytic activity (50% lysis) of rt-Pa in 1:10 diluted PPP from citrated blood.

Examples of standard curves of fibrinolytic activity (50% lysis) of rt-PA are shown in FIG. 2.

FIG. 2a shows a standard curve in 1:10 diluted PPP from EDTA blood.

FIG. 2b shows a standard curve in 1:10 diluted PPP from citrated blood.

It will be appreciated that the standard curves are not linear over the entire measuring range from 2 to 1000 ng/ml. At lower dosages of rt-PA, such as are used for the indication "deep vein thrombosis", plasma levels of only 2 to 40 mg/ml can be expected. The course of the curve in this narrow range should be regarded as linear.

A particularly preferred embodiment of the entire test is therefore divided into the following individual steps:

a) Sampling of citrated or EDTA blood before the beginning of fibrinolytic therapy in order to plot a standard curve.

b) Obtaining platelet poor plasma (PPP) and diluting the PPP 1:10 with a suitable diluent.

c) Plotting a standard curve for this dilute PPP by adding the plasminogen activator in concentrations ranging from 2 to 1,000 ng/ml, preferably 2 to 100 ng/ml.

d) Repetition of a) and b) during fibrinolytic therapy.

e) Determining the current fibronolytic overall activity in the patient's plasma by means of the standard curve.

Using the results obtained, the quantity of plasminogen activator infused can be corrected if necessary in order to obtain the desired overall fibrinolytic activity in the patient's blood.

The individual steps are preferably carried out as follows:

a) The blood sample is taken under the usual conditions. EDTA blood: 1 part 2% EDTA+9 parts blood. Citrated blood: 1 part 3.8% sodium citrate+9 parts blood.

b) The blood is centrifuged for 15 minutes at 3300×g and at 20° C. immediately after being taken. After centrifuging, the supernatant PPP is removed and diluted 1:10.

Diluent for PPP obtained from EDTA blood: 2% polyethyleneglycol 10,000 with a molecular weight in the range from 9,000 to 12,500 and 0.1% Tween 80 in physiological saline solution.

Diluent for PPP from citrated blood: 2% polyethyleneglycol 10,000 with a molecular weight in the range from 9,000 to 12,500, 0.1% Tween 80 and 0.02% EDTA in physiological NaCl solution.

c) As an example of a plasminogen activator, rt-PA was used (Actilyse), whilst in order to dilute the rt-PA the following buffer was used: 0.5 M L-arginine, 0.1% Tween 80 and 0.05 M $Na_2HPO_4$, pH 7.4.

In order to plot the standard curve, the lysis activities in the concentration range from 2 to 1000 ng/ml of rt-PA in PPP from EDTA for citrated blood with the compositions of the individual test were determined according to the following plan (rt-PA final concentration in PPP in order to plot the standard curve):

1000 ng/ml, 800 ng/ml, 600 ng/ml, 400 ng/ml, 200 ng/ml, 100 ng/ml, 80 ng/ml, 60 ng/ml, 40 ng/ml, 20 ng/ml, 10 ng/ml, 8 ng/ml, 6 ng/ml, 4 ng/ml and 2 ng/ml If necessary, the range of concentration may be made narrower or broader or fewer measuring points may be determined.

d) and e) In order to determine the fibrinolytic state of a patient under therapy, 0.1 ml of PPP, obtained from the patient's blood, is diluted with 0.9 ml of one of the above-mentioned suitable diluents and after mixing the mixture is incubated for 5 minutes at 37° C. Then 50 μl of batroxobin are added and after mixing the change in turbidity is recorded photometrically at a wavelength of 340 nm. Using the standard curve, the concentration of plasminogen activator corresponding to the fibrinolytic activity in the plasma can be determined from the time taken to reach 50% lysis.

If the fibrinolytic activity does not correspond to the intended level, this may be corrected by adapting the rate of infusion of he plasminogen activator accordingly.

A further advantage o the method according o the invention is that it is also suitable for determining low concentrations of plasminogen activator in the presence of heparin. This is of major importance in fibrinolytic therapy since this is normalcy carried out using heparin as well.

To demonstrate this advantage, the influence of heparin on the lysis time was tested as follows:

In the test according to the invention, heparin was added to citrated or EDTA plasma according to the following plan:

a) citrated PPP

| 8 ng/ml rt-PA Heparin E/ml Lysis 50% in min. | Citrated - PPP | | | | |
|---|---|---|---|---|---|
| | 0 | 0.1 | 1 | 5 | 10 |
| 1 | 28.67 | 31.30 | 31.00 | 30.67 | 39.33 |
| 2 | 27.33 | 28.67 | 30.67 | 31.67 | 31.67 |
| Mean value | 28.00 | 29.99 | 30.94 | 31.17 | 35.50 | b) EDTA-PPP

| 8 ng/ml rt-PA Heparin E/ml Lysis 50% in min. | EDTA - PPP | | | | |
|---|---|---|---|---|---|
| | 0 | 0.1 | 1 | 5 | 10 |
| 1 | 27.00 | 26.00 | 26.67 | 29.00 | 31.00 |
| 2 | 24.00 | 23.33 | 25.67 | 25.67 | 25.67 |
| Mean value | 25.50 | 26.67 | 26.17 | 27.34 | 28.33 |

Figure 3A:
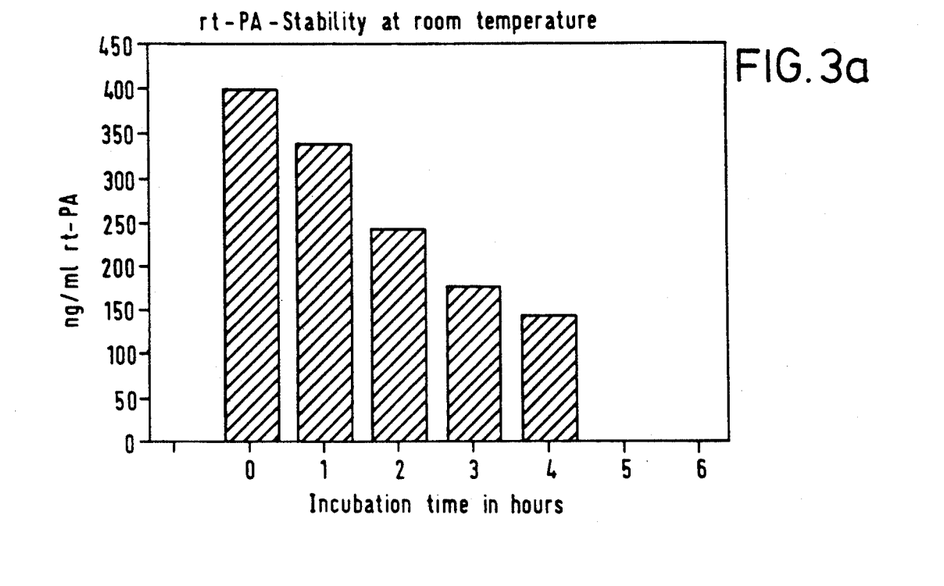
FIGS. 3a and 3b show the decrease in measurable fibrinolytic activity when he blood sample is stored at room temperature.
Figure 3B:
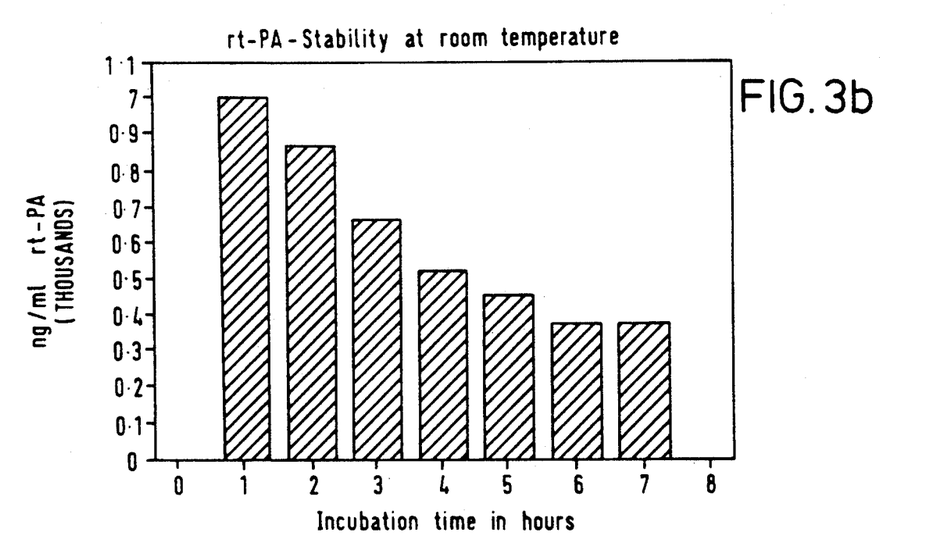
Figure 4A:
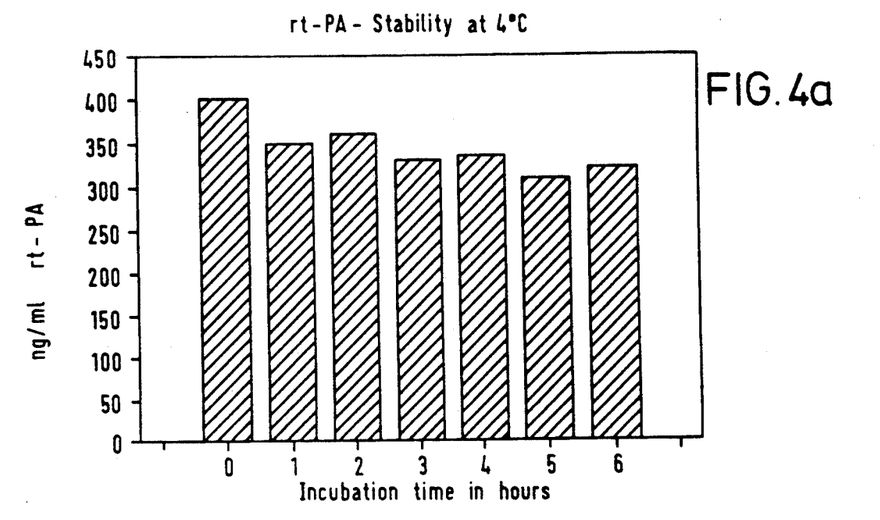
FIGS. 4a and 4b show the decrease in measurable fibrinolytic activity when the blood sample is stored at 4° C.
Figure 4B:
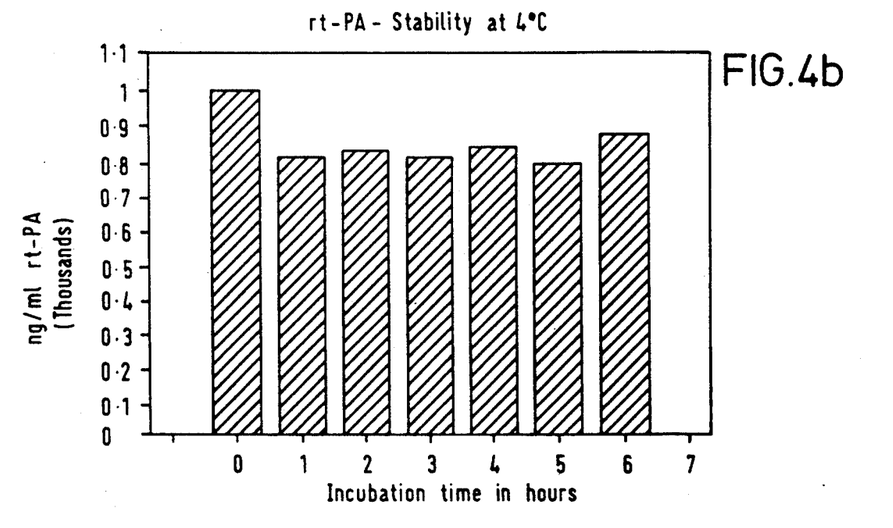

If the sample cannot be prepared and measured immediately after the blood sample is taken, the plasma should be stored at 4° C. since at ambient temperature (RT) the measurable fibrinolytic activity decreases rapidly (FIGS. 3a and 3b). At 4° C. this loss is restricted to about 20% within one hour and does not increase any further in the following 5 hours (FIGS. 4a and 4b), so that the measurements obtained can be corrected to allow for this loss. Measurements taken at a later stage are unusable since they do not allow the infusion to be corrected in order to adjust the fibrinolytic activity within a reasonable period of time.

Figure 5A:
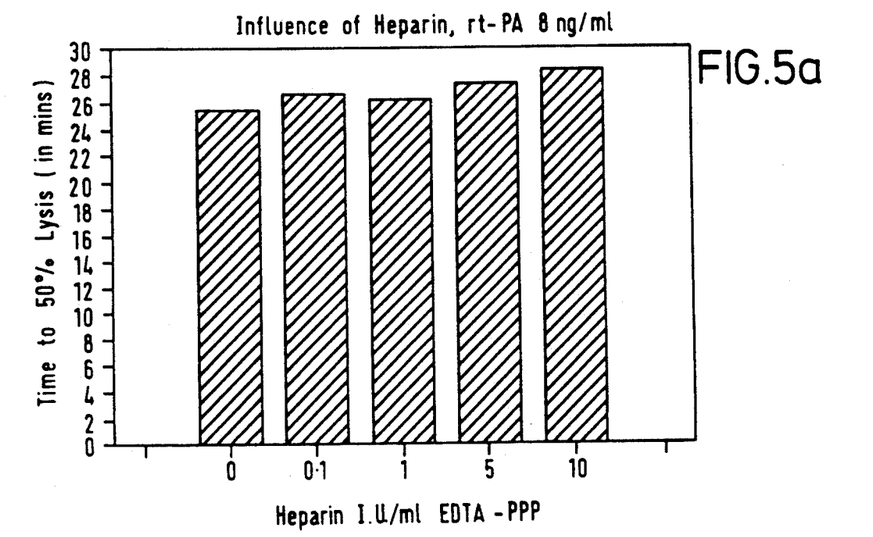
FIGS. 5a and 5b show the effect of the addition of heparin on the time to achieve 50% lysis.
Figure 5B:
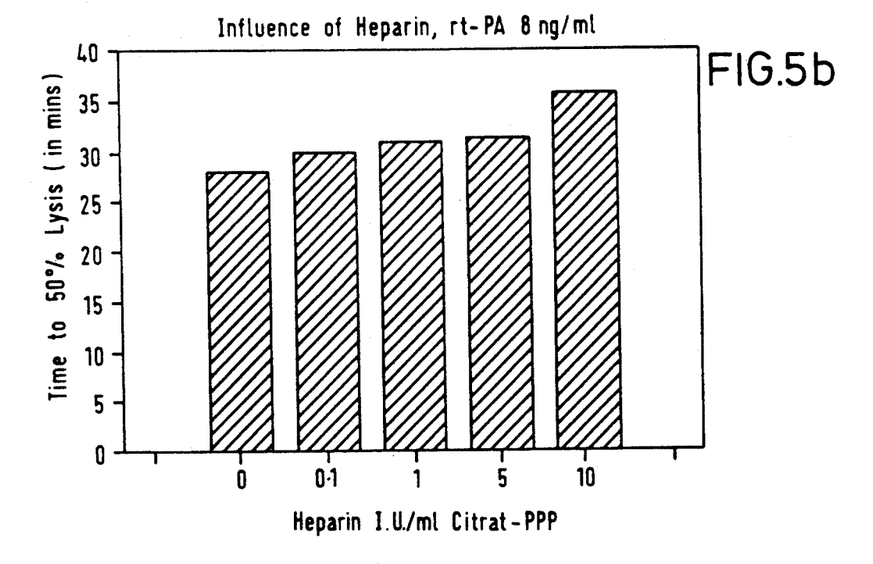

Furthermore, FIGS. 5a and 5 show that even when the rt-PA concentration are very low the effect of the addition of heparin up to 1 E/ml is relatively small, i.e. the time taken to achieve 50% lysis or the end of lysis is not significantly lengthened or shortened ($\leq 10\%$).

Figure 6:
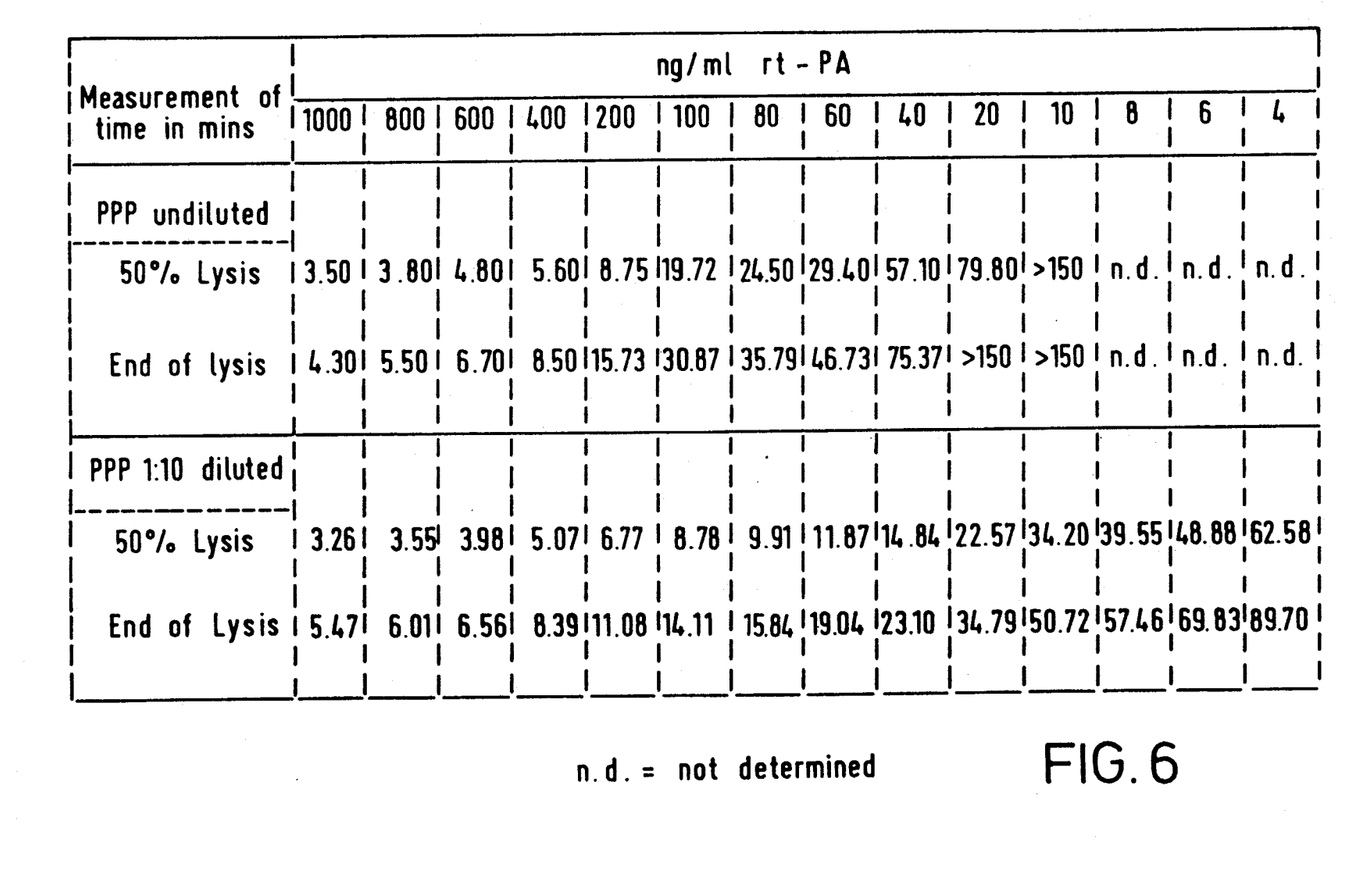
FIG. 6 shows the effectiveness of the method of this invention for determining fibrinolytic activity.

The superiority of the method of determination according to the invention is clear from FIG. 6:

Samples which have very long lysis times in the undiluted state (50% lysis or end of lysis) and which therefore cannot be measured according to the methods of DE-A-3,502,878 (50% lysis takes more than 3 hours), can easily be determined using the methods according to the invention, since the measuring time needed, particularly for low concentrations of plasminogen activator, can be substantially shortened.

This is of major importance in carrying out measurements during a therapy, which are effected using low concentrations of plasminogen activator, e.g. in the treatment of deep-vein thrombosis, lung embolism, etc.

Moreover, when the process according to the invention is carried out using physiological saline solution as diluent and with the addition of 2% by weight of commercial polyethyleneglycol 10,000, having an average molecular weight of 9,000 to 12,500, there is no undesirable retraction in the sample.

The Example which follows illustrates the invention in conjunction with the foregoing description and the accompanying drawings:

EXAMPLE

Reagents

Reptilase: 20 PU/ml
rt-PA: (2 to 1000 ng/ml solely as a control)
Dilution buffer for citrated PPP:
  0.9% sodium chloride solution
  2.0% polyethyleneglycol 10,000
  0.1% Tween 80
  0.02% EDTA
Dilution buffer for EDTA-PPP:
  0.9% sodium chloride solution
  2.0% polyethyleneglycol 10,000
  0 1% Tween 80

Test composition:

10 μl rt-PA (2 to 1000 ng solely as a control)
100 μl PPP

Dilution buffer for the citrate blood: physiological NaCl-solution 2% Polyethyleneglycol 10,000 0.1% Tween 80 0.02% EDTA Dilution buffer for the EDTA-blood: physiological NaCl-solution 2% Polyethyleneglycol 1,000 0.1% Tween 80

PROCEDURE

Preparation of plasma

Blood was extracted in the normal way from the Vena cubitalis. It was then immediately subjected to centrifugation at 3300×g (4,000 rpm) for 15 minutes at 20 C. PPP was then removed.

Figure 1:
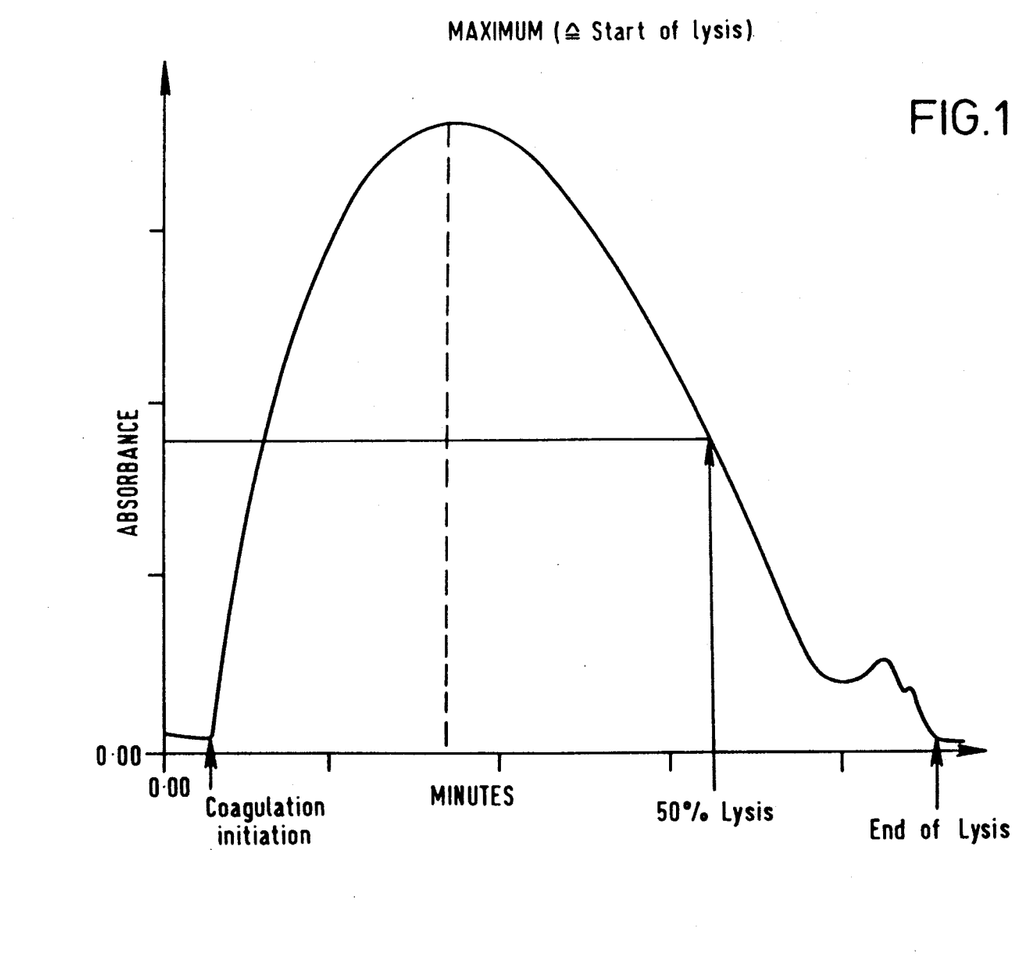
FIG. 1 shows a graph which depicts the measurement of fibrinolytic activity as the time from the start of coagulation until 50% lysis is achieved, in relation to the peak coagulation.

Preparation of the rt-PA-Standard (see FIG. 1)

The lysis activity of the following rt-PA concentrations in respectively citrate-PPP and EDTA-PPP was determined: 1,000, 800, 600, 400, 200, 100, 80, 60, 40, 20, 8, 6, 4 and 2 ng/ml. The rt-PA dilution were obtained by means of arginine buffer in accordance with the following table:

| Amount of rt-PA solution | Concentration of rt-PA solution | + 0.5M Arginine buffer | = Concentration of the rt-PA solution | Amount added to 1 ml PPP | rt-PA concentration in PPP |
|---|---|---|---|---|---|
| 50 μl | 1 mg/ml | 450 μl | 100 μg/ml | 10 μl | 1000 ng/ml |
| 40 μl | 1 mg/ml | 460 μl | 80 μg/ml | 10 μl | 800 ng/ml |
| 30 μl | 1 mg/ml | 470 μl | 60 μg/ml | 10 μl | 600 ng/ml |
| 20 μl | 1 mg/ml | 480 μl | 40 μg/ml | 10 μl | 400 ng/ml |
| 10 μl | 1 mg/ml | 490 μl | 20 μg/ml | 10 μl | 200 ng/ml |
| 50 μl | 100 μg/ml | 450 μl | 10 μg/ml | 10 μl | 100 ng/ml |
| 50 μl | 80 μg/ml | 450 μl | 8 μg/ml | 10 μl | 80 ng/ml |
| 50 μl | 60 μg/ml | 450 μl | 6 μg/ml | 10 μl | 60 ng/ml |
| 50 μl | 40 μg/ml | 450 μl | 4 μg/ml | 10 μl | 40 ng/ml |
| 50 μl | 20 μg/ml | 460 μl | 2 μg/ml | 10 μl | 20 ng/ml |
| 50 μl | 10 μg/ml | 450 μl | 1 μg/ml | 10 μl | 10 ng/ml |
| 50 μl | 8 μg/ml | 450 μl | 0.8 μg/ml | 10 μl | 8 ng/ml |
| 50 μl | 6 μg/ml | 450 μl | 0.6 μg/ml | 10 μl | 6 ng/ml |
| 50 μl | 4 μg/ml | 450 μl | 0.4 μg/ml | 10 μl | 4 ng/ml |
| 50 μl | 2 μg/ml | 450 μl | 0.2 μg/ml | 10 μl | 2 ng/ml |

300 μl diluent (0.9% sodium chloride solution+2.0% polyethyleneglycol 10,000)

The sample is thoroughly mixed, incubated for 5 minutes at 37° C., then combined with 50 μl of reptilase and mixed thoroughly once more.

After coagulation has been initiated the increase and decrease in extension is immediately monitored photometrically at a wavelength of 340 nm and a measuring temperature of 37° C.

CONSTRUCTION OF A GRAPH SHOWING THE RT-PA-DISOS ACTIVITY RELATIONSHIP IN THE 1:10 AND 1:20 DILUTED CITRATE - AND EDTA-PPP

Reagents

Reptilase (Boehringer Mannheim, Order No. 1265650): Contents of each Vial should be dissolved in 1 ml distilled water.
Citrate blood: 1 part 3,8% sodium citrate+9 parts blood
EDTA blood: 1 part 2% EDTA+9 parts blood
rt-PA-Standard: lmg/ml
  0.5 M arginine buffer pH 7.4:
  0.5 M L-Arginine
  0.1% Tween 80
  0.05 M Disodiumhydrogen-phosphate

KIT FOR USE IN DETERMINING FIBRINOLYTIC ACTIVITY IN A HUMAN PLASMA SAMPLE

A) For 3×20 determinations in citrate-Plasma (1-part 3.8% sodium citrate+9 parts blood)

Reagents 60 ml dilution buffer:
  0.9% NaCl solution
  2% Polyethylene glycol 10,000
  0.1% Tween 80
  0.02% EDTA
3×20 PU/vial Reptilase (dissolve the content of one vial in +1 ml distilled water) (PU - Plough Units)
rt-PA standard: 1 mg pro ml
50 ml Arginine buffer (for dilution of the rt-PA standard):
  0.5 M L-Arginine pH 7.4
  0.% Tween 80
  0.5 M Disodiumhydrogenphosphate B) For 3×20 determinations in EDTA-Plasma (1 part 2% EDTA+1 part blood):

Reagents:

60 ml dilution buffer:
  0.9% NaCl solution

2% Polyethyleneglycol 10,000
0.1 Tween 80
3×20 PU/Vial Reptilase (dissolve the content of one vial in 1 ml distilled water)
rt-PA standard: 1 mg pro ml
50 ml Arginine buffer (for dilution of the rt-PA standard):
0.5 M L-Arginine pH 7.4
0.1% Tween 80
0.5 M Disodiumhydrogenphosphate

What is claimed is:

1. In a method for determining the total dibrinolytic activity of the plasma in a patient's blood wherein
   a) a sufficient quantity of fibrin to produce turbidity is added to a native sample of the plasma or generated in situ and the turbidity or the fibrin cleavage products formed is or are measured: or
   b) a chromogenic plasma substrate and a quantity of fibrin, fibrinogen cleavage products or an enzyme which produces turbidity, are added to a native sample of the plasma and the color formed is measured, the improvement which comprises substituting a dilute platelet poor sample of the plasma for the native sample of the plasma and adding 1 to 5 percent by weight of polyethylene glycol with a molar weight of 8000 to 35,000.

2. A method as recited in claim 1, wherein the polyethylene glycol has a molecular weight of about 9000 to 12,500.

3. A method as recited in claim 1, wherein the concentration of the polyethylene glycol is about 2 percent by weight.

* * * * *